(12) United States Patent
Lin et al.

(10) Patent No.: US 8,110,605 B2
(45) Date of Patent: Feb. 7, 2012

(54) COMPOUND FOR INACTIVATING VIRUSES AND BACTERIA AND METHOD OF MAKING SAME

(75) Inventors: Shiming Lin, Taipei (TW); Chih-Kung Lee, Taipei (TW); Shih-Yuan Lee, Taipei (TW); Jim-Tong Hong, Taipei County (TW); Ming-Chu Cheng, Taipei County (TW); Chih-Chen Lin, Fengshan (TW); Rong-Sin Wu, Banqiao (TW); Shu-Fang Chu, Yilan (TW); Yu-Ting Chang, Sanchong (TW); Wen-Ching Ko, Kaohsiung (TW)

(73) Assignee: National Taiwan University, Taipei (TW)

( * ) Notice: Subject to any disclaimer, the term of this patent is extended or adjusted under 35 U.S.C. 154(b) by 107 days.

(21) Appl. No.: 12/710,460

(22) Filed: Feb. 23, 2010

(65) Prior Publication Data

US 2011/0015435 A1 Jan. 20, 2011

(30) Foreign Application Priority Data

Jul. 14, 2009 (TW) .............................. 98123749 A (51) Int. Cl.
*A61K 31/20* (2006.01)
*B32B 5/12* (2006.01)
(52) U.S. Cl. .......................................... 514/558; 442/59
(58) Field of Classification Search ........................ None
See application file for complete search history.

(56) References Cited

FOREIGN PATENT DOCUMENTS
WO WO 01/35906 A2 * 5/2001

OTHER PUBLICATIONS

Simard et al, Medicinal Chemistry, Reversible Regulation of Chymotrypsin Activity Using Negatively Charged Gold Nanoparticles Featuring Malonic Acid Terminii, 2005, 1, pp. 153-157.*

* cited by examiner

*Primary Examiner* — Paul A Zucker
(74) *Attorney, Agent, or Firm* — Bacon & Thomas, PLLC (57) ABSTRACT

The invention discloses a novel compound effective in inactivating viruses and bacteria. The compound, 2-(10-mercaptodecyl)-propanedioic acid or salts thereof, is shown to disrupt, break down or inactivate viruses and bacteria, thus suppressing infection and proliferation thereof in host cells. A method of chemically synthesizing the novel compound is also disclosed.

14 Claims, 3 Drawing Sheets

COMPOUND FOR INACTIVATING VIRUSES AND BACTERIA AND METHOD OF MAKING SAME

BACKGROUND OF THE INVENTION

1. Field of the Invention

This invention relates in general to a substance for disinfecting virus and bacteria and, in particular, to a chemical substance that digests and disinfects virus and bacteria so as to break them down and suppress their infection to host cells and proliferation. The present invention also relates to a method for producing such substance.

2. Technical Background

Microbes such as virus and bacteria are microorganisms responsible for many diseases, many of which are fatal to human if infected. Various medical treatments including vaccination and drug cures are available for human in the defense against known microbes. However, for known or unknown virus and bacteria alike for which no known defense or cure are available are fierce enough to inflict high mortality and are capable of efficient infection schemes such as airborne transmission, the first and only effective means for protection is disinfection.

Disinfection of virus and bacteria can be achieved physically, chemically and biochemically. Physical disinfection schemes include heating, drying, freezing, radioactive irradiation and filtration, etc. These physical disinfection schemes are relatively constrained in terms of factors such as characteristics of environments in which to perform such processing. Chemical and biochemical disinfection schemes are thus more practically applicable for defense against virus and bacteria.

Materials and substances generally used as chemical or enzymatic disinfectants include acid, alkaline, alcohol, carbolic acid, formaldehyde, surfactants, halogen, heavy metals, dyes oxidants and protease etc. in principle, they achieve microorganism disinfection chemically or enzymatically via one or more of four of the following effects: damages to envelope/membrane, destruction of cellular transportation, viral/bacterial protein digestion/denaturing, and enzyme reactivity and/or receptor affinity suppression.

Effectiveness of chemical/enzymatic disinfectants is varied. In principle, the more effective is a chemical/enzymatic disinfectant, the more hazardous it is likely to human. Selection of disinfectants depends on factors including the type of the target microbe, characteristics of the site to apply disinfection, and disease prevention requirements, among others.

In general, an ideal chemical/enzymatic disinfectant should qualify the following characteristics: effectiveness against a broad variety of microbes; negligible susceptibility to organic compounds, superior viral/bacterial surface destructive capability; non-corrosive, non-toxic and non-irritative to human; chemical/biochemical stability with accelerated disinfecting effectiveness; high water solubility; sustained adherence to the surface of the disinfected object for sustained viral/bacterial suppression capability; and reasonable cost for mass production.

SUMMARY OF THE INVENTION

With the foregoing in mind, the present invention advantageously provides a compound effective in breaking down virus and bacteria so as to suppress their infection to host cells and subsequent proliferation. The invention acts by digestion of viral and/or bacterial structures by the action of 2-(10-mercaptodecyl)-propanedioic acid or salts thereof. To achieve break down virus and bacteria, the present invention provides a compound that comprises a 2-(10-mercaptodecyl)-propanedioic acid according to the formula:

Formula 1

$$HS-(CH_2)_g-CH(COOH)_2$$

Figure 1:
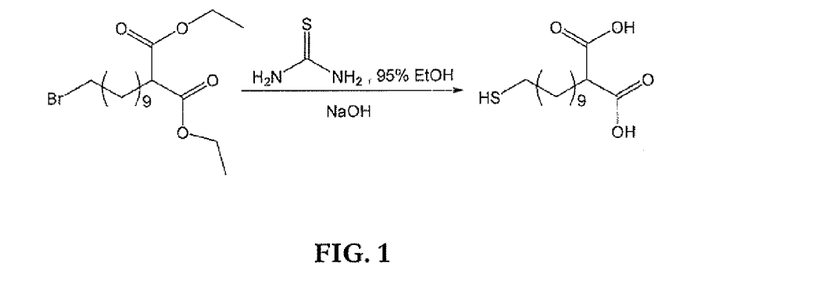
FIG. 1 shows a chemical reaction for synthesizing the compound of the present invention, 2-(10-mercaptodecyl)-propanedioic acid.
Figure 2:
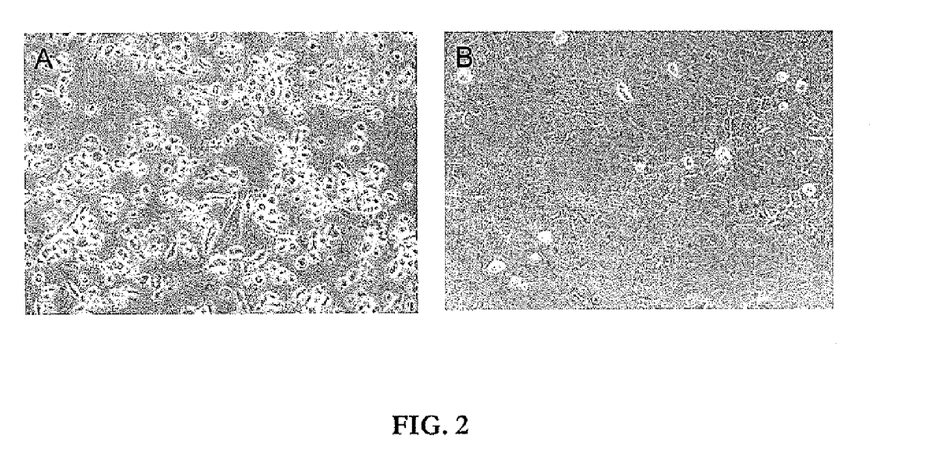
FIG. 2 provides microscopic images of Madin-Darby canine kidney cells infected by influenza virus H1N1 subtype, before and after treatment with the compound of the invention.

The present invention also provides a process for producing 2-(10-mercaptodecyl)-propanedioic acid according to the reaction scheme as shown in FIG. 1.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENTS

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

The inventive compound has been shown to be effective in disrupting viral/bacterial structures to inactivate viruses that possess an envelope (e.g., influenza virus H1N1, H5N1 and H5N2 subtypes) as well as those that do not (e.g., *Enterovirus* type 71) and, in addition, infective bacteria as well (e.g., *Staphylococcus*).

The present invention promotes breakdown of viruses and bacteria to thereby suppress viral infection to host cells and bacterial proliferation through the use of 2-(10-mercaptodecyl)-propanedioic acid or salts thereof to inactivate these microorganisms.

The present invention also provides a method for making the 2-(10-mercaptodecyl)-propanedioic acid. Synthesis of the presently disclosed compound is based on the chemical reaction shown in FIG. 1. The method of synthesis comprises reacting ethyl 2-(10-bromo-decyl)malonate with thiourea and ethanol and then with aqueous sodium hydroxide. A preferred embodiment of the synthesis is as follows.

Reflux a solution of ethyl 2-(10-bromo-decyl)malonate (5.5 mmole) and thiourea (6.6 mmole) in 95% ethanol (25 mL) for 5 hours and then add an aqueous NaOH (2.0 M, 25 mL) and reflux for another 15 hours. Then, add an aqueous HCl (2.0 M) until the solution becomes acidic (approximately pH ~2). Extract the reaction mixture with ether three times and wash and dry the combined organic layers with saturated NaCl solution with $MgSO_4$. The product, 2-(10-mercaptodecyl)-propanedioic acid, can then be obtained by removal of solvent under reduced pressure.

The inventive compound 2-(10-mercaptodecyl)-propanedioic acid or salts thereof is capable of partially or completely disrupting the envelope/membrane proteins of the virus and bacteria and destroying their binding sites for the host cells to thereby suppress their infective ability and their proliferation.

To be effective in breaking down virus and bacteria, preferably, the inventive compound 2-(10-mercaptodecyl)-propanedioic acid or salts thereof should best be employed as a solution of, for example, $H_2O$, C1-C3 alcohol, tetrahydrofuran (THF), dimethyl sulfoxide (DMSO) or any mixture thereof but not limited thereto. More preferably, the inventive compound 2-(10-mercaptodecyl)-propanedioic acid or salts thereof should be dissolved in a mixture of ethanol and water.

Concentration of 2-(10-mercaptodecyl)-propanedioic acid or salts thereof in a solution should range from about 30 to 1,000 ppm to be effective in suppressing viral/bacterial infection of host cells and subsequent proliferation of these microorganisms. When the concentration of 2-(10-mercaptodecyl)-propanedioic acid is less than about 30 ppm, effective disinfection may not be achieved. However, when the concentration is more than about 1,000 ppm, the inventive compound becomes cytotoxic to host cells. Accordingly, preferred concentrations for antimicrobial effectiveness of the compound has been determined to range from about 45 to 750 ppm.

Based on the structure of its outer infective surface, a virus can be grouped in one of two classes: (1) enveloped viruses and (2) naked viruses, that is, viruses without an envelope. Both types of viruses were found to be susceptible to the disruptive effect of the present compound. Infection of host cells and subsequent proliferation of these flu viruses can be effectively suppressed through the use of the inventive compound and salts thereof. These influenza viruses include Spanish flu virus, Asian flu virus, Hong Kong flu, avian influenza, swine flu virus and their recombinant variants. Extensive laboratory experiments have been conducted and the results show that the compound of the present invention can effectively break down influenza virus H1N1, avian influenza virus H5N1 and H5N2 subtypes to suppress their infection to host cells and proliferation. Moreover, the inventive compound has no cytotoxicity for host cells, a toxicity that can result in cell deform, lysis or apotosis.

The inventive compound 2-(10-mercaptodecyl)-propanedioic acid or salts thereof can disrupt non-enveloped Enteroviruses to suppress their infection to host cells and subsequent proliferation. Enteroviruses are small RNA picornaviridae. Contraction of *Enterovirus* type 71 often leads to neurological complications. In laboratory experiments, the compound of the present invention has been shown effective in disrupting *Enterovirus* type 71 so as to suppress its infectiveness for host cells and subsequent proliferation. Moreover, the inventive compound causes no cytotoxicity in the host cell.

The inventive compound 2-(10-mercaptodecyl)-propanedioic acid or salts thereof can also inactivate bacterial pathogens such as *Staphylococcus* and prevent its proliferation. There are as many as 26 subtypes of *Staphylococci*, among which *Staphylococcus aureus, Staphylococcus epidermidis* and *Staphylococcus saprophyticus* are common infectious agents in the hospital setting. These are frequently the cause of surgical site infections and various systemic infections. In laboratory experiments, the compound of the present invention effectively suppressed *Staphylococcus aureus* infection and proliferation.

The term "host cell" as used herein refers to a living cell in which a virus reproduces and includes a human cell. In the description context of the present invention, host cells also include those from non-human sources, for example, avians including poultry or migratory birds; mammalian including murine, caprine, bovine, porcine or equine; primates including monkeys, apes and especially chimpanzees; or other animals as well. Likewise, the term "living organism" as used herein refers to the source organisms for the above cells.

In the description context of the present invention, "contacting the viruses or bacteria outside of living organisms or cells" means exposing the target virus or bacteria to 2-(10-mercaptodecyl)-propanedioic acid or salts thereof outside of a living organism or a cell, in an environment such as a test tube or Petri dish or in a natural environment such as in air or on an environmental surface.

According to the present invention, effectiveness of the inventive compound in breaking down, disrupting or inactivating viruses and bacteria so as to suppress their infectivity and ability to proliferate is effected by contacting the target microorganism with 2-(10-mercaptodecyl)-propanedioic acid or salts thereof outside of living organisms or cells.

In accordance with the present invention, to break down or disrupt viral or bacterial agents in order to suppress their infectivity and therefore subsequent proliferation in or on a host cell, the inventive compound 2-(10-mercaptodecyl)-propanedioic acid or salts thereof can be incorporated, for example, in personal hygiene products such as feminine napkins or public sanitation products such as toilet cleaners and floor and surface cleaners, products for air sanitizing or air freshening, or be coated on or incorporated in fabrics used to make protective products such as face masks, protective clothes and air filters, among others. When used in personal hygiene, public sanitation or air cleaning/freshening or personal hygiene products such as hand sanitizers, liquid hand wash, shower gels, shampoos or air spray, the inventive compound 2-(10-mercaptodecyl)-propanedioic acid or salts thereof can be contained in a composition together with other additives based on their respective professional preparation protocols, particularly in pharmaceutically acceptable compositions and with the guidance provided by such treatises as United States Pharmacopeia or the National Formulary.

When used on fabrics, 2-(10-mercaptodecyl)-propanedioic acid or salts thereof can be added directly to fibrous materials used to produce such fabrics. Fibrous materials applicable include high-molecular-weight non-woven material, natural fibers or their mixtures, among others.

Experimental Data Showing Disinfection Efficacy

The inventive compound 2-(10-mercaptodecyl)-propanedioic acid or salts thereof have been tested in various laboratory experiments for an evaluation of the effectiveness of their designed functionality, namely, the ability via disinfection to suppress bacterial/viral infection to host cells and consequent proliferation. The following are the results of several experiments.

Experiment 1: Suppression of Influenza Virus H1N1 Subtype

MDCK cells ($5\times10^5$ cells) were cultured on 6-well plates (Nunc). Influenza virus H1N1 subtype (A/WSN/33) (from ATCC, USA) with titer of $1\times10^5$ PFU/mL (one milliliter of inoculum contains $10^5$ virions and can infect approximately 50% of the cells) was added to 500 μL 2×MEM (minimum essential medium) containing fetal bovine serum, the non-essential amino acid L-glutamine and penicillin/streptomycin.

The compound 2-(10-mercaptodecyl)-propanedioic acid was dissolved in ethanol liquid (ethanol:water=1:10) to obtain solutions with final concentrations of 0, 6, 20, 60, 200, 600, 2,000 and 6,000 ppm. These solutions were each mixed with an equal volume of the virus solution and incubated at room temperature (~25° C.) for 30 minutes. In this experiment, the concentration of viral medium and 2-(10-mercaptodecyl)-propanedioic acid thus became half that of the original 5 concentration.

The control is 2-(10-mercaptodecyl)-propanedioic acid mixed with an equal 2× growth MEM without virus. In this control, the concentration of growth medium and 2-(10-mercaptodecyl)-propanedioic acid thus became half that of the original concentration.

Then, the above mixtures were added into MDCK cells and incubated at 37° C. After 2 hours, the cells were washed with P135 (phosphate buffered saline, Invitrogen) to remove unbound viruses. Two milliliters per well of 1×MEM without fetal bovine serum were added and incubated for 36 hours at 37° C. CPE (cytopathic effects) were observed under a reverse microscope (Zeiss). The cells with CPE became rounded-up, detached from the plate and

TABLE 1

Efficacy of 2-(10-mercaptodecyl)-propanedioic acid against H1N1 influenza virus

| | | 2-(10-mercaptodecyl)-propanedioic acid (ppm) | | | | | | | |
|---|---|---|---|---|---|---|---|---|---|
| | | 0 | 3 | 10 | 30 | 100 | 300 | 1,000 | 3,000 |
| Subtype of H1N1 influenza virus treated with 2-(10-mercaptodecyl)-propanedioic acid | CPE | + | + | +/− | − | − | − | CTX | CTX |
| 2-(10-mercaptodecyl)-propanedioic acid only | CPE | − | − | − | − | − | − | CTX | CTX |

+: Viral activity
ctx = cytotoxicity
−: No viral activity eventually died. Table 1 summarizes the efficacy of the inventive compound 2-(10-mercaptodecyl)-propanedioic acid against H1N1 influenza virus in three independent experiments.

The above results show that the inventive compound 2-(10-mercaptodecyl)-propanedioic acid is capable of protecting cells against infection by influenza virus H1N1 subtype with a concentration as low as 30 ppm. The control shows that 2-(10-mercaptodecyl)-propanedioic acid causes no cytotoxicity when the concentration is smaller than 300 ppm. Cytotoxicity occurred only at concentrations exceeding 1,000 ppm.

Experiment 2: Suppression of Tamiflu™-Resistant H1N1 5 Influenza Virus

MDCX cells ($5\times10^5$ cells) were cultured on 6-well plates (Nunc). Tamiflu™-resistant strain H1N1 influenza virus (A/TW/066/09) (from ATCC, USA) with a titer of $7\times10^5$ PFU/ml (one ml medium contains $10^5$ virus and can infect approximately 50% of cells) was added to 500 μL 2×MEM medium which contains Fetal bovine serum, non-essential amino acid L-glutamine and penicillin/streptomycin.

The compound 2-(10-mercaptodecyl)-propanedioic acid was dissolved in ethanol liquid (ethanol:water=1:10) to have final concentrations of 0, 6, 20, 60, 200, 600, 2,000 and 6,000 ppm. These solutions were each mixed with an equal volume of virus and incubated at room temperature (~25° C.) for 30 minutes. In this experiment, the concentration of viral medium and 2-(10-mercaptodecyl)-propanedioic acid thus became half that of the original concentration.

The control is 2-(10-mercaptodecyl)-propanedioic acid mixed with equal 2× growth MEM medium without virus. In this control, the concentration of growth medium and 2-(10-mercaptodecyl)-propanedioic acid thus became half that of the original concentration.

Then, the above mixtures were added into MDCX cells and incubated at 37° C. After 2 hours, the cells were washed with PBS (phosphate buffered saline, Invitrogen) to remove unbound viruses. Two milliliters per well of 1×MEM medium without fetal bovine serum were added and incubated for 36 hours at 37° C. CPE was observed under a reverse microscope (Zeiss). The cells with CPE became round-up and detached from plate and eventually died.

Table 2 shows the efficacy of 2-(10-mercaptodecyl)-propanedioic acid against Tamiflu™-resistant H1N1 strain in three independent experiments.

TABLE 2

Efficacy of 2-(10-mercaptodecyl)-propanedioic acid against Tamiflu™-resistant H1N1 influenza virus

| | | 2-(10-mercaptodecyl)-propanedioic acid (ppm) | | | | | | | |
|---|---|---|---|---|---|---|---|---|---|
| | | 0 | 3 | 10 | 30 | 100 | 300 | 1,000 | 3,000 |
| Tamiflu™-resistant H1N1 influenza virus treated with 2-(10-mercaptodecyl)-propanedioic acid | CPE | + | + | +/− | − | − | − | CTX | CTX |
| 2-(10-mercaptodecyl)-propanedioic acid only | CPE | − | − | − | − | − | − | CTX | CTX |

+: Viral activity
CTX = cytotoxicity
−: No viral activity

In the above experimental results, 2-(10-mercaptodecyl)-propanedioic acid is demonstrated to be able to protect cells against infection by Tamiflu™-resistant H1N1 influenza virus with a concentration as low as 30 ppm. The control shows that the 2-(10-mercaptodecyl)-propanedioic acid causes no cytotoxicity when the concentration is less than 300 ppm. Cytotoxicity occurred only at concentrations exceeding 1,000 ppm.

Experiment 3: Disruption of Tamiflu™-Resistant Influenza Virus H1N1

For atomic force microscopic (AFM) studies, virions of Tamiflu™-resistant H1N1 subtype influenza virus (A/TW/066/09) were attached to the surface of a mica substrate. This was done through electrostatic interaction by placing the virions in contact with a freshly cleaved mica that had been coated with poly-L-lysine hydrobromide, a positively charged compound.

After cleaning the mica with methanol and Milli-Q water, a drop of 0.01% (wt/vol) poly-L-lysine hydrobromide solution was applied and incubated for 30 minutes. The mica surface was then washed with Milli-Q water before introduction of the H1N1 specimen. The specimen was applied onto the treated mica for 5 min at room temperature, followed by washing with distilled water (50 μL, 3 times) and drying in air prior to the AFM experiment.

Figure 3:
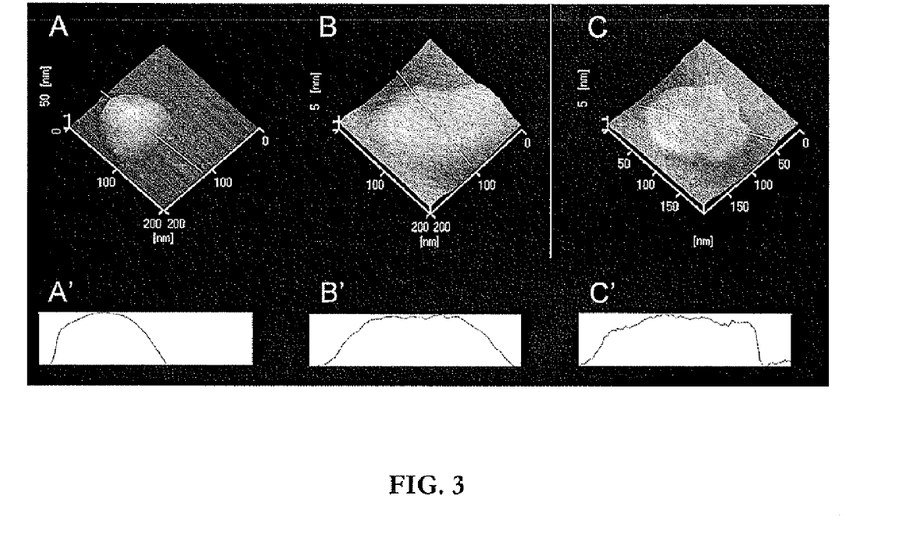
FIG. 3 shows the surface ultrastructure of different single H1N1 swine flu virus particles revealed by atomic force microscopy before (first column) and after (second to third column) treatment by the inventive compound, 2-(10-mercaptodecyl)-propanedioic acid, together with 10 corresponding cursor profiles (second row) that provide quantitative measurements of H1N1 virion dimensions.

AFM experiments in tapping mode operation were carried out using a multimode scanning probe microscope (SPI300 HV, Seiko Instruments Inc., Chiba, Japan) in combination with an optical microscope. AFM tips were 200 μm long and had a typical resonant frequency of 140 kHz (Nanosensor, Wetzlar-Blankenfeld, Germany). Light tapping was used, which involved maintaining a high amplitude reference relative to the free amplitude of the cantilever. Scanning began typically on a 20 μm×20 μm area that contained hundreds of H1N1 virions. Gradually, imaging size was reduced to isolate individual virion (200 nm×200 nm). H1N1 specimen were scanned in both directions several times before capturing an image in order to ensure that tip artifacts, such as hysteresis, were not interfering with the imaging. Over 60 high-quality images were captured for each H1N1 virion, from which a number of images were selected. One of such images is as shown in FIG. 3A. When a line was drawn across the image, the topography of the sample as a function of vertical distance from the mica substrate surface was displayed, such as in FIG. 3A'. These height tracing were performed to provide more information on how each treatment affected the surface topography of the 5 virus particle.

Then, the mica substrate adsorbed with H1N1 virions was washed with Milli-Q water before treatment by the inventive compound 2-(10-mercaptodecyl)-propanedioic acid. 10 μL of 30 and 300 ppm solutions of the inventive compound in distilled water were introduced to the mica substrate, respectively, followed by incubation for 5-10 minutes prior to AFM experiments.

Native H1N1 virions in an environment of distilled water and that were completely intact served as a control (FIG. 3A). When viruses were exposed to the inventive compound 2-(10-mercaptodecyl)-propanedioic acid, their viral morphology was apparently affected, as is shown in FIGS. 3B and 3C—H1N1 virions treated respectively with 30 and 300 ppm of the inventive compound 2-(10-mercaptodecyl)-propanedioic acid displayed ultrastructures with heterogeneous surfaces. The native virion (FIG. 3A) was disrupted and somewhat flattened as is readily observed in FIGS. 3B and 3C.

Moreover, the inventive compound 2-(10-mercaptodecyl)-propanedioic acid caused a substantial reduction in the surface height and irregularity in the viral surfaces. The corresponding cursor profiles (FIGS. 3A'-3C') provide quantitative measurements of the dimensions of the viral surface nanostructures. Profiles displayed in FIGS. 3A'-3C' show that the maximum height of particles as measured were approximately 54.16, 6.95 and 5.28 nm, respectively. Over 60 virus particles treated with the inventive compound were examined.

Although some variations exist in the exact height of these particles, the surface traces were, however, reproducible. Calculated RMS height values of particles treated with 30 and 300 ppm of the inventive compound were 7.09±0.42 and 5.39±0.23 nm respectively.

Experiment 4: Suppression of Avian Influenza Virus H5N1 Subtype

MDCK cells were cultured on 96-well plates (Nunc). The tested subtype of H5N1 avian influenza virus (TW1209/03 (H5N1)AIV) (Animal Health Research Institute, Taiwan) has a titer of $1 \times 10^7$ $EID_{50}/0.1$ mL (defined as 0.1 mL medium contains $10^7$ virus that can infect 50% of cells) or 64 HAU/25 μL (defined as 25 μL medium contains 64 hemagglutinins).

2-(10-mercaptodecyl)-propanedioic acid was dissolved in ethanol liquid (ethanol:water=1:10) to have final concentrations of 0, 6, 20, 60, 200, 600, 2,000 and 6,000 ppm. These solutions were each mixed with an equal volume of virus and incubated at room temperature (~25° C.) for 30 minutes. In this experiment, concentration of viral medium and 2-(10-mercaptodecyl)-propanedioic acid thus became half that of the original concentration.

The control is 2-(10-mercaptodecyl)-propanedioic acid mixed with equal 2× growth MEM without virus. In this control, concentration of growth medium and 2-(10-mercaptodecyl)-propanedioic acid thus became half that of the original concentrations.

Then, the 100 μL mixtures were added into MDCK cells and incubated at 37° C., respectively. After 2 hours, the cells were washed with MEM (GIBCO) to remove unbound viruses. 100 μL per well of 1×MEM medium were added and incubated for 7 days at 37° C. CPE were observed under a reverse microscope (Nikon). The cells with CPE became roundedup and detached from plate and eventually died. At the same time, hemagglutination activity was measured and 50 μL per well of MEM medium were added into 25 μL of chicken red blood cell 15 suspension, CRBC suspension in PBS buffer. The data of hemagglutination assay (HA) was observed to quantify of the viruses by hemagglutination. Table 3 shows the HA testing in three independent experiments.

TABLE 3

Efficacy of 2-(10-mercaptodecyl)-propanedioic acid against H5N1 avian influenza virus

| | | 2-(10-mercaptodecyl)-propanedioic acid (ppm) | | | | | | |
|---|---|---|---|---|---|---|---|---|
| | | 0 | 3 | 10 | 30 | 100 | 300 | 1,000 | 3,000 |
| Subtype of H5N1 avian influenza virus treated with 2-(10-mercaptodecyl)-propanedioic acid | CPE | + | + | + | + | − | − | CTX | CTX |
| | HA | + | + | + | + | − | − | CTX | CTX |
| 2-(10-mercaptodecyl)-propanedioic acid only | CPE | − | − | − | − | − | − | CTX | CTX |

+: Viral activity
CTX = cytotoxicity
−: No viral activity

TABLE 4

Efficacy of 2-(10-mercaptodecyl)-propanedioic acid against H5N2 avian influenza virus

| | | 2-(10-mercaptodecyl)-propanedioic acid (ppm) | | | | | | |
|---|---|---|---|---|---|---|---|---|
| | | 0 | 3 | 10 | 30 | 100 | 300 | 1,000 | 3,000 |
| Subtype of H5N2 avian influenza virus treated with 2-(10-mercaptodecyl)-propanedioic acid | CPE | + | + | + | + | − | − | CTX | CTX |
| | HA | + | + | + | + | − | − | CTX | CTX |
| 2-(10-mercaptodecyl)-propanedioic acid only | CPE | − | − | − | − | − | − | CTX | CTX |

+: Viral activity
CTX = cytotoxicity
−: No viral activity

In the above result, the 2-(10-mercaptodecyl)-propanedioic acid with a concentration above 1,000 ppm was shown to be able to protect cells against H5N1 influenza virus infection. This demonstrates that the drug can inhibit the virus. In the control, when 2-(10-mercaptodecyl)-propanedioic acid was ≦300 ppm, no cytotoxicity was caused. Cytotoxicity occurred only when the concentration exceeds 1,000 ppm.

The HA testing shows that the 2-(10-mercaptodecyl)-propanedioic acid with a concentration above 1,000 ppm can protect RBC cells to sustain no agglutination. This demonstrates that the drug can inhibit the H5N1 virus.

Experiment 5: Suppression of Avian Influenza Virus H5N2 Subtype

MDCK cells were cultured on 96-well plates (Nunc). Tested was the subtype of H5N2 avian influenza virus (TW1209/04(H5N2)AIV) (Animal Health Research Institute, Taiwan) with titer of $1 \times 10^7$ $EID_{50}$/0.1 mL (defined as 0.1 mL medium contains $10^7$ virus and can infect 50% of the cells) or 64 HAU/25 µL (defined as 25 µL medium contains 64 hemagglutinins).

2-(10-mercaptodecyl)-propanedioic acid was dissolved in ethanol liquid (ethanol:water=1:10) to have final concentrations of 0, 6, 20, 60, 200, 600, 2,000 and 6,000 ppm. These solutions were each mixed with an equal volume of virus and incubated at room temperature (~25° C.) for 30 minutes. In this experiment, the concentration of viral medium and 2-(10-mercaptodecyl)-propanedioic acid thus became half that of the original concentration.

The control is 2-(10-mercaptodecyl)-propanedioic acid mixed with equal 2× growth MEM medium without virus. In this control, the concentration of growth medium and 2-(10-mercaptodecyl)-propanedioic acid thus became half that of the original concentration.

Then, the 100 µL mixtures were added into MDCK cells and incubated at 37° C., respectively. After 2 hours, the cells were washed with MEM (GIBCO) to remove unbound viruses.

100 µL per well of 1×MEM were added and incubated for 7 days at 37° C. CPE were observed with a reverse microscope (Nikon). The cells with CPE became rounded up and detached from the plate and eventually died. At the same time, hemagglutination activity was measured and 50 µL per well of MEM medium were added into 25 µL of chicken red blood cell suspension, CRBC suspension in PBS buffer. The data of hemagglutination assay (HA) was observed to quantify of the viruses by hemagglutination.

Table 4 shows the HA testing in three independent experiments.

In this result, the 2-(10-mercaptodecyl)-propanedioic acid can protect cells against H5N2 influenza virus infection with concentration above 1,000 ppm, demonstrating that the drug can inhibit virus by interacting with virus. In the control, when 2-(10-mercaptodecyl)-propanedioic acid was ≦300 ppm, no cytotoxicity was caused. Cytotoxicity occurred only when concentration exceeds 1,000 ppm.

From the HA testing, 2-(10-mercaptodecyl)-propanedioic acid with concentration above 1,000 ppm is shown to be able to protect RBC cells to sustain no agglutination. This demonstrates that the drug can inhibit the virus by interacting with the H5N2 viruses.

Experiment 6: Breaking Down of Influenza Virus H5N2 Subtype

For AFM studies, avian influenza virus (AIV) subtype H5N2 (TW1209/04(H5N2)AIV) sample virions were attached to the surface of a mica substrate. This was done through electrostatic interaction by placing the virions in contact with a freshly cleaved mica that had been coated with poly-L-lysine hydrobromide, a positively charged compound.

After cleaning the mica with methanol and Milli-Q water, a drop of 0.01% (wt/vol) poly-L-lysine hydrobromide solution was applied and incubated for 30 minutes. The mica surface was then washed with Milli-Q water before introduction of the H5N2 specimen. The specimen was applied onto the poly-L-lysine-treated mica for 5 minutes at room temperature, followed by washing with distilled water (50 µL, 3 times) and drying in air prior to the AFM experiments.

Figure 4:
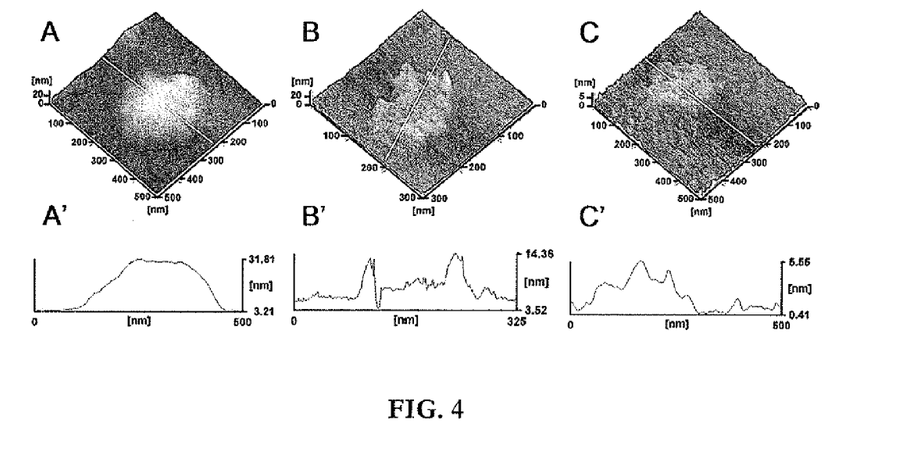
FIG. 4 shows the surface ultrastructure of different single avian influenza virus (AIV) particles revealed by atomic force microscopy before (first column) and after (second to third column) treatment by the inventive compound, 2-(10-mercaptodecyl)-propanedioic acid, together with corresponding cursor profiles (second row) that provide quantitative measurements of AIV virion dimensions.

AFM experiments in tapping mode of operation were carried out using a multimode scanning probe microscope (SPI300 HV, Seiko Instruments Inc., Chiba, Japan) in combination with an optical microscope. AFM tips were 200 µm long and had a typical resonant frequency of 140 kHz (Nanosensor, Wetzlar-Blankenfeld, Germany). Light tapping was used, which involved maintaining a high amplitude reference relative to the free amplitude of the cantilever. Scanning began typically on a 20 µm×20 µm area that contained hundreds of H5N2 virions. Gradually, imaging size was reduced to isolate individual virion (300 nm×300 nm). H5N2 specimen were scanned in both directions several times before capturing an image, in order to ensure that tip artifacts, such as hysteresis, were not interfering with the imaging. Over 60 high-quality images were captured for each H5N2 virion, from which a number of images were selected. One of such images is as shown in FIG. 4A. When a line was drawn across the image, the topography of the sample as a function of vertical distance from the mica surface was displayed (FIG.

4A'). These height traces were collected to provide more information on how each treatment affected the surface topography.

Then, the mica substrate adsorbed with H5N2 virions was washed with Milli-Q water before introduction of the inventive compound 2-(10-mercaptodecyl)-propanedioic acid. 10 μL of 100 and 1,000 ppm solutions of the inventive compound in distilled water were introduced onto the mica substrate, respectively, followed by incubation for 5-10 minutes prior to the AFM experiments.

Native H5N2 virions in the environment of distilled water were completely intact and served as a control (FIG. 4A). When the viruses were exposed to the inventive compound 2-(10-mercaptodecyl)-propanedioic acid, their viral morphology was apparently affected, as is shown in FIGS. 4B and 4C—H5N2 virions treated respectively with 100 and 1,000 ppm 2-(10-mercaptodecyl)-propanedioic acid displayed ultrastructures with heterogeneous surfaces. The native virion (FIG. 4A) was broken down and flattened as is readily observed in FIGS. 4B and 4C.

Moreover, the inventive compound 2-(10-mercaptodecyl)-propanedioic acid caused a substantial reduction in the surface height and irregularity in the viral surfaces. The corresponding cursor profiles (FIGS. 4A'-4C) provide quantitative measurements of the dimensions of the surface nanostructures. Profiles displayed in FIGS. 4A'-4C' show that the maximum height of particles as measured were approximately 31.81, 14.36 and 5.55 nm, respectively. Over 60 virus particles treated with the inventive compound were examined. Although some variations exist in the exact height of these treated particles, the surface traces were, however, reproducible. Calculated RMS height values of particles treated with 100 and 1,000 ppm of the inventive compound were 14.29±0.87 and 5.62±0.53 nm respectively.

Experiment 7: Breaking Down of *Enterovirus* Type 71

For AFM studies, *Enterovirus* type 71 (EV-71) sample virions were attached to a mice substrate. This was done through electrostatic interaction by placing the virions in contact with an freshly cleaved mica that had been coated with poly-L-lysine hydrobromide, a positively charged compound.

After cleaning the mica with methanol and Milli-Q water, a drop of 0.01% (wt/vol) poly-L-lysine hydrobromide solution was applied and incubated for 30 minutes. The mica surface was then washed with Milli-Q water before introduction of the EV-71 specimen. The specimen was applied onto the poly-L-lysine-treated mica for 5 minutes at room temperature, followed by washing with distilled water (50 L, 3 times) and drying in air prior to the AFM experiments.

Figure 5:
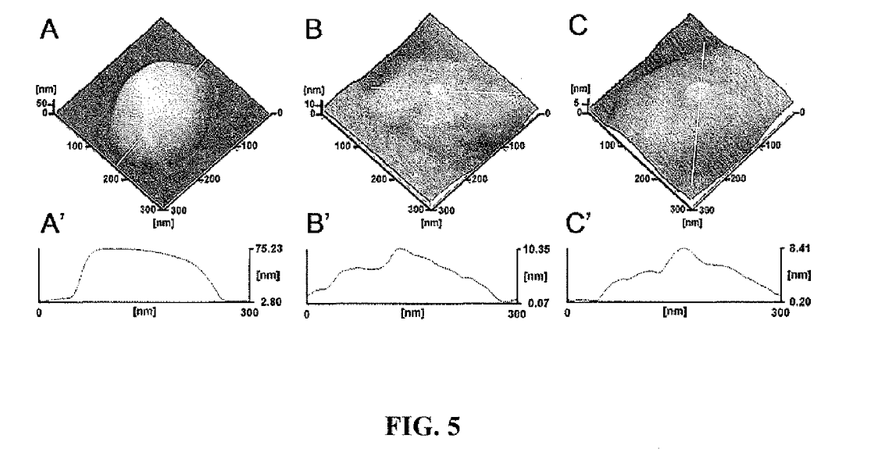
FIG. 5 shows the surface ultrastructure of different single *Enterovirus* type 71 (EV-71) virions revealed by atomic force microscopy before (first column) and after (second to third column) treatment by the inventive compound 2-(10-mercaptodecyl)-propanedioic acid, together with corresponding cursor profiles (second row) that provide quantitative measurements of EV-71 virion dimensions.

AFM experiments in tapping mode operation were carried out using a multimode scanning probe microscope (SPI300 HV, Seiko Instruments Inc., Chiba, Japan) in combination with an optical microscope. AFM tips were 200 μm long and had a typical resonant frequency of 140 kHz (Nanosensor, Wetzlar-Blankenfeld, Germany). Light tapping was used, which involved maintaining a high amplitude reference relative to the free amplitude of the cantilever. Scanning began typically over a 20 μm×20 μm area that contained hundreds of EV-71 virions. Gradually, imaging size was reduced to isolate individual virion (300 nm×300 nm). EV-71 specimen were scanned in both directions several times before capturing an image in order to ensure that tip artifacts, such as hysteresis, were not interfering with the imaging. Over 60 high-quality images were captured for each EV-71 virion, from which a number of images were selected. One of such images is as shown in FIG. 5A. When a line was drawn across the image, the topography of the sample as a function of vertical distance from mica surface was displayed, such as is shown in FIG. 5A'. These height traces were collected to provide more information on how each treatment affected the virion surface topography.

Then, the mica substrate adsorbed with EV-71 virions was washed with Milli-Q water before introduction of the inventive compound 2-(10-mercaptodecyl)-propanedioic acid. 10 μL of 30 and 1,000 ppm solutions of the inventive compound in distilled water were introduced to the mica substrate, respectively, followed by incubation for 5-10 minutes prior to AFM experiments.

EV-71 virions in the environment of distilled water were completely intact and served as a control (FIG. 5A). When viruses were exposed to the inventive compound 2-(10-mercaptodecyl)-propanedioic acid, their viral morphology was apparently affected, as is shown in FIGS. 5B and 5C—EV-71 virions treated respectively with 30 and 1,000 ppm 2-(10-mercaptodecyl)-propanedioic acid displayed ultrastructures with heterogeneous surfaces. The native virion (FIG. 5A) was broken down and flattened as can be readily observed in FIGS. 5B and 5C.

Moreover, the inventive compound 2-(10-mercaptodecyl)-propanedioic acid caused a substantial reduction in the surface height and irregularity in the viral surfaces. The corresponding cursor profiles (FIGS. 5A'-5C') provide quantitative measurements of the dimensions of the viral surface nanostructures. Profiles displayed in FIGS. 5A'-5C' show that the maximum height of virus particles measured were approximately 75.23, 10.35 and 8.41 nm, respectively. Over 60 virus particles treated with the inventive compound were examined. Although some variations exist in the exact height of such particles, the surface traces were, however, reproducible. Calculated RMS height values of particles treated with 30 and 1,000 ppm of the inventive compound were 10.49±0.52 and 8.35±0.63 nm respectively.

Experiment 8: Proliferation Suppression of *Staphylococcus Aureus*

*Staphylococcus aureus* strain (ATCC-25923) was grown aerobically at 37° C. in LB broth and on the agar plate. *S. aureus*-25923 in the logarithmic phase of growth were harvested to a tube with LB broth medium at 37° C. and incubated overnight (about 12~18 hours), then centrifuged under 3,000 rpm for 10 minutes, washed two times with PBS (pH=7.2) and diluted with the same buffer. Then, the cell concentration of *S. aureus*-25923 was quantitated by ultraviolet-visible spectrophotometry (UV-VIS analysis) to the optical density of ca. 0.1 at 620 nm, corresponding to $10^4$ colony-forming units (CFU)/mL and provided for susceptibility testing.

Antibacterial effects of the inventive compound 2-(10-mercaptodecyl)-propanedioic acid were evaluated by the determination of minimum inhibitory concentration (MIC) using the broth dilution method. Tubes containing 500 μL of *S. aureus* in LB broth and 2-(10-mercaptodecyl)-propanedioic acid in 10% (v/v) ethanol/D.I. water ranging from 5 to 200 μg/mL were reacted with $10^4$ CFU/mL of *S. aureus*. Thereafter, 100 μL of *S. aureus* were drawn from each of the tubes, inoculated evenly onto the LB nutrient agar plate and incubated at 37° C. for 12~18 hours. The number of bacterial colonies was counted and the percentage of *S. aureus* suppressed was calculated. To determine the degree of the antibacterial effect in the presence of the inventive compound 2-(10-mercaptodecyl)-propanedioic acid, the number of remaining *S. aureus* was examined three times.

TABLE 5

Antibacterial effects of 2-(10-mercaptodecyl)-propanedioic acid against *Staphylococcus aureus*

| | Final concentration of 2-(10-mercaptodecyl)-propanedioic acid (ppm) | | | | | | |
|---|---|---|---|---|---|---|---|
| | 0 | 5 | 10 | 20 | 50 | 100 | 200 |
| MIC of *S. aureus* | + | + | + | − | − | − | − |

+: Proliferation of *S. aureus*,
−: Antibacterial effect of *S. aureus*

Table 5 shows that proliferation of *S. aureus* was suppressed by using 20 ppm final concentration 2-(10-mercaptodecyl)-propanedioic acid.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A composition for breaking down virus and bacteria comprising:

30~1000 ppm of a 2-(10-mercaptodecyl)-propanedioic acid according to the formula:

a carrier.

2. The composition of claim 1, wherein said 2-(10-mercaptodecyl)-propanedioic acid is in the form of a salt thereof.

3. The composition of claim 1, wherein said carrier is water, C1-C3 alcohol, tetrahydrofunan, dimethyl sulfoxide or mixture thereof.

4. The composition of claim 1 wherein said virus is H1N1 virus.

5. The composition of claim 1 wherein said virus is H5N1 virus.

6. The composition of claim 1 wherein said virus is H5N2 virus.

7. The composition of claim 1 wherein said virus is *Enterovirus* type 71 virus.

8. The composition of claim 1 wherein said bacteria is *Staphylococcus*.

9. A personal hygiene product comprising said composition of claim 1.

10. An air cleaning product comprising the composition of claim 1.

11. A public sanitation product comprising the composition of claim 1.

12. A fabric material comprising the composition of claim 1.

13. A personal protective product comprising the fabric of claim 12.

14. The personal protective product of claim 13, wherein the personal protective product is a garment.

* * * * *